(12) United States Patent
Slemker et al.

(10) Patent No.: US 6,358,453 B1
(45) Date of Patent: Mar. 19, 2002

(54) MODULAR DISTAL PLATE FOR RAPID MANUFACTURING OF A PROSTHETIC LIMB SOCKET

(75) Inventors: Tracy C. Slemker, Clayton; Scott R. Schall, Englewood, both of OH (US)

(73) Assignee: Prosthetic Design, Inc., Clayton, OH (US)

( * ) Notice: Subject to any disclaimer, the term of this patent is extended or adjusted under 35 U.S.C. 154(b) by 0 days.

(21) Appl. No.: 09/288,331

(22) Filed: Apr. 8, 1999

Related U.S. Application Data
(60) Provisional application No. 60/081,190, filed on Apr. 9, 1998.

(51) Int. Cl.$^7$ .............................................. B29C 33/40
(52) U.S. Cl. ........................ 264/222; 264/308; 623/33; 623/901
(58) Field of Search .......................... 264/5, 274, 222, 264/308; 623/901, 33, 34

(56) References Cited

U.S. PATENT DOCUMENTS

| | | | |
|---|---|---|---|
| 4,749,347 A | 6/1988 | Valavaara | 425/135 |
| 5,121,329 A | 6/1992 | Crump | 364/468 |
| 5,163,965 A | * 11/1992 | Rasmusson et al. | 623/33 |
| 5,303,141 A | 4/1994 | Batchelder et al. | 364/149 |
| 5,340,433 A | 8/1994 | Crump | 156/578 |
| 5,426,722 A | 6/1995 | Batchelder | 395/80 |
| 5,491,643 A | 2/1996 | Batchelder | 364/512 |
| 5,503,785 A | 4/1996 | Crump et al. | 264/40.7 |
| 5,587,913 A | 12/1996 | Abrams et al. | 364/468.26 |
| 5,662,715 A | 9/1997 | Slemker | 623/36 |
| 5,728,168 A | * 3/1998 | Laghi et al. | 623/33 |

OTHER PUBLICATIONS

Rolock & Tucker, Squirt Shape, Jan. 1998.
Swanson, The World in the Palm of Your Hand, Spring 1993.

* cited by examiner

*Primary Examiner*—Bruce Snow
(74) *Attorney, Agent, or Firm*—Taft, Stettinius & Hollister LLP

(57) ABSTRACT

The present invention facilitates the use of the rapid manufacturing systems in the manufacture of prosthetic limb sockets by providing a substantially flat and strong distal attachment plate or base for the deposition of the fused-deposition-modeling materials thereon. The present invention also provides a method for fabricating a socket of a prosthetic limb which comprises the steps of: (a) providing a substantially flat distal attachment plate, where the attachment plate includes a coupling mechanism carried thereon for coupling a prosthetic upright assembly thereto; and (b) repeatedly depositing layers of solidifying material to the proximal surface of the attachment plate, controlled, at least in part, according to the dimensions of the patient's residual limb, so as to form a socket for receiving the patient's residual limb. The attachment plate may have a notch machined or formed into its proximal surface, about a periphery thereof, for receiving a first layer of the solidifying material and providing at least two bonding surfaces for the solidifying material.

8 Claims, 9 Drawing Sheets

MODULAR DISTAL PLATE FOR RAPID MANUFACTURING OF A PROSTHETIC LIMB SOCKET

CROSS REFERENCE TO RELATED APPLICATIONS

The present application claims priority under 35 U.S.C. §119 from U.S. Provisional Patent Application, Ser. No. 60/081,190, filed Apr. 9, 1998.

BACKGROUND

The present invention relates generally to prosthetic devices and, more particularly, to a component for facilitating rapid manufacturing of a prosthetic limb socket using fused deposition modeling or another similar multi-layer rapid fabrication technology.

A prosthesis is often used to replace an amputated portion of a limb and to help restore the amputee's ability to use that limb. A prosthesis for a lower extremity amputation will often include an artificial foot connected to an upright assembly (pylon, tube or shaft) which is in turn connected to a custom fitted socket assembly. If the amputation is an above the knee amputation, the upright assembly will commonly include an artificial knee joint.

Such prosthetic devices typically include an outer socket made from a hard thermoplastic material. The outer sockets are conventionally created by heating a thermoplastic preform cone or a thermoplastic sheet, stretching the heated plastic over a positive mold of the socket (which is typically a modified positive cast of the amputee's residual limb), and then vacuum forming the plastic in place over the positive mold.

In the field of prosthetics, the use and implementation of computer aided design and manufacturer (CAD/CAM) is becoming more and more prevalent, especially in the design and fabrication of the positive molds for the prosthetic limb sockets. See, for example, U.S. Pat. No. 5,824,111 to Schall. Presently, CAD/CAM systems are effective in digitizing an impression of the amputee's residual limb, modifying the digital model using a CAD software design package, and then milling a positive mold of the socket on a computer numerically controlled (CNC) milling or carving machine based upon this modified digital model. Additionally, with the advent of such CAD/CAM systems, the use of modular endo-skeletal components, such as interconnection components for coupling the prosthetic limb socket to the upright assembly, is also becoming more and more prevalent. See, for example, U.S. Pat. No. 5,662,715.

U.S. Pat. No. 5,662,715 to Slemker discloses a modular interconnection component for a prosthetic limb assembly that resides within the distal end of the prosthetic limb socket. The component includes four holes bored into its distal end for receiving bolts extending from an attachment plate of an upright assembly into the distal end of the socket. Because the interconnection component and the attachment plate act to "sandwich" the distal end wall of the socket, it is extremely important that this distal end wall be substantially flat and very strong. It is also important that the transition from the distal end walls to the side wall of the socket be substantially strong.

Another advancement currently being developed in the prosthetics field is the utilization of rapid prototyping technology in the fabrication of prosthetic limb socket. An example of such rapid prototyping technology is Fused Deposition Modeling (FDM), commercially available from Stratasys Inc. FDM is described in substantial detail in U.S. Pat. No. 5,121,329 to Crump. Generally, this process utilizes a CAD system for creating a digitized geometric model of an object. The three-dimensional dimensions of this object are then sent to a deposition apparatus which is designed to deposit multiple layers of a heated thermoplastic material (in a fluid state) onto a base so as to build a three dimensional version of the object as directed by the dimensions. Preferably, the material solidifies substantially instantaneously upon extrusion or dispensing onto the base, with the build up of multiple layers forming the desired object.

Therefore, rather than transmitting dimensions of a prosthetic limb socket mold to a CNC milling or carving machine to create a socket mold, the fabricator is able to transmit the dimensions of the finished socket to the FDM system, which will then create the finished socket in minutes. This general concept is also described in the Slemker '715 patent.

One known difficulty in incorporating FDM in the fabrication of prosthetic limb sockets is the inability for FDM to provide substantially flat distal end walls of the socket as discussed above. Because the FDM system is designed to stack multiple layers of solidifying material on top of one another, a flat and strong horizontal surface is difficult to manufacture. For example, the system disclosed in the Crump patent extrudes heated plastic strands of material in a rectangular formation (longer sides are oriented on top and bottom) and the layer by layer overlap creates a bond between the layers. Accordingly, to provide the strongest structure, it is preferred that the layers are stacked upon one another. Therefore, it is difficult for this system to create a horizontal flat surface that is strong enough for use as a distal end of a prosthetic limb socket.

Accordingly, a need exists for facilitating the use of the rapid manufacturing systems in the manufacture of prosthetic limb sockets, which provides a substantially flat and extremely strong distal end surface of the prosthetic limb socket such that the modular interconnection components can be used.

SUMMARY

The present invention facilitates the use of the rapid manufacturing systems in the manufacture of prosthetic limb sockets by providing a substantially flat and strong distal attachment plate or base for the deposition of the FDM materials thereon. The present invention also provides a method for fabricating a socket of a prosthetic limb which comprises the steps of:

(a) providing a substantially flat distal attachment plate, where the attachment plate includes a coupling means carried thereon for coupling a prosthetic upright assembly thereto; and (b) repeatedly depositing layers of solidifying material to the proximal surface of the attachment plate, controlled, at least in part, according to the dimensions of the patient's residual limb, so as to form a socket for receiving the patient's residual limb. The attachment plate is preferably flat and rigid and includes a notch extending into the proximal surface and substantially about an outer periphery of the attachment plate so that, in step (b) above, at least one layer of the solidifying material is deposited into the notch so that the notch provides at least two faces for the first layer of solidifying material to bond to.

Accordingly, a prosthetic limb socket fabricated in such a manner will have a strong and substantially flat distal surface for coupling the endoskeletal prosthetic limb components thereto. Furthermore, the present invention facilitates the use of CAD systems and rapid manufacturing systems to fabricate prosthetic limb sockets in under an hour.

In one embodiment of the invention, the notch machined into the attachment plate is a helical notch, starting at a circumferential point at a first depth and ending at the circumferential point at a second depth, deeper than the first depth. Accordingly, the material deposited into the helical notch may build upon itself in a continuous helical layer.

Preferably, the attachment plate includes a plurality of bolt-receiving holes extending therethrough, and arranged in a standard four-hole pattern, for facilitating the coupling of a pyramid attachment plate to the distal surface of the socket.

Additionally, the rapid manufacturing system can be adapted to deposit two or more different types of material, at least one which hardens to be a substantially rigid material and another which hardens to be a material that is more flexible. Accordingly, the rapid manufacturing unit can be controlled to deposit the more rigid materials in portions of the socket that require greater support and strength and can deposit the less rigid and more flexible materials in portions of the socket that require less strength or that provide comfort to the patient's residual limb.

DETAILED DESCRIPTION

Figure 1:
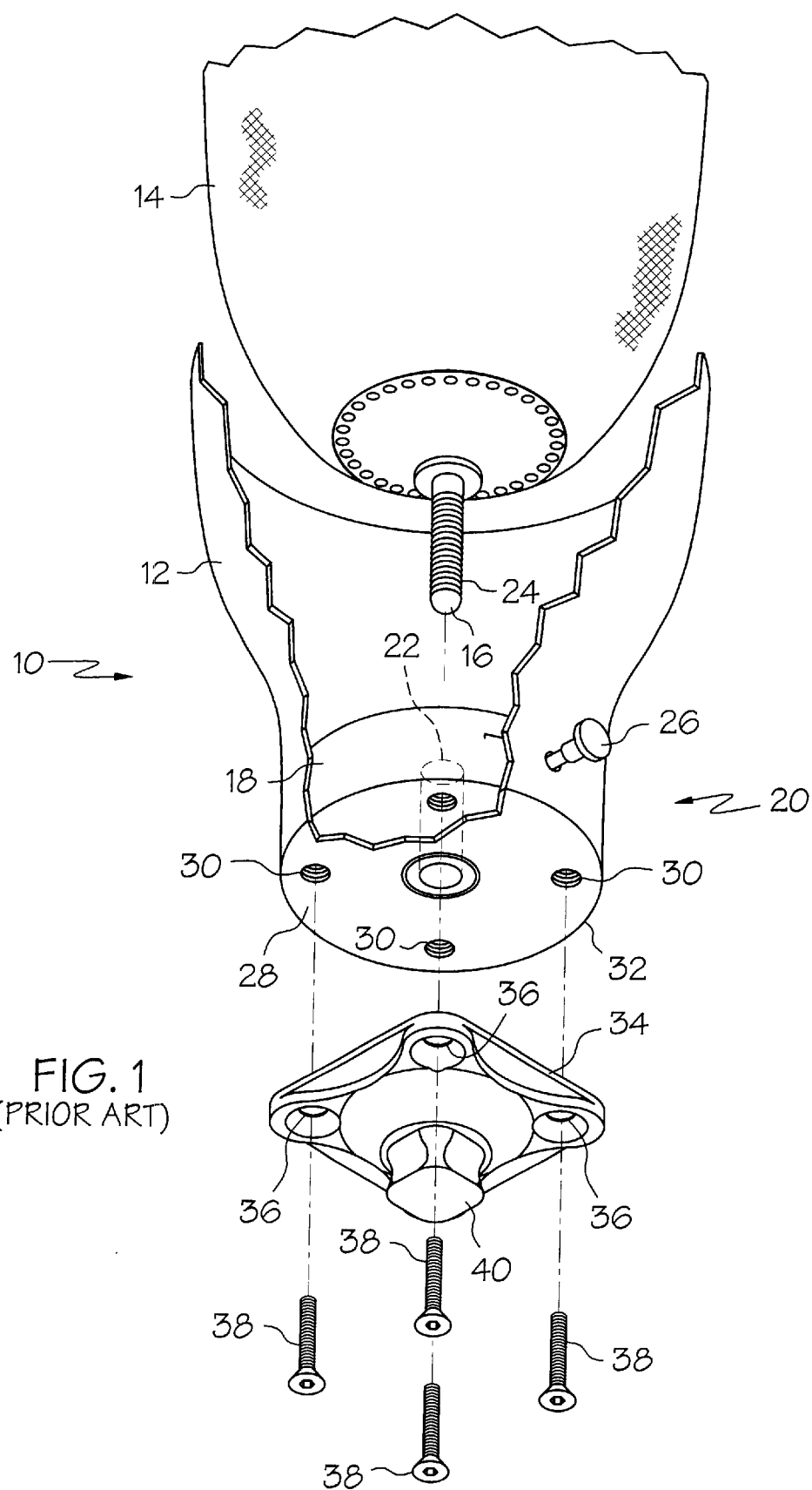
FIG. 1 is a perspective view of a conventional prosthetic limb socket assembly, incorporating off-the-shelf interconnection components.

As shown in FIG. 1, a conventional socket assembly will consist of a hard plastic outer socket 12 and a soft, resilient inner sleeve 14. The inner sleeve is formed to snugly fit over the residual limb of the patient, and to provide comfort to the residual limb of the patient when the prosthetic limb is worn by the patient. The inner sleeve 14 has a locking pin 16 formed integrally therewith and extending from the distal end of the sleeve. The locking pin at 16 is adapted to engage with a locking mechanism within a universal lock 18 releasably positioned within an extended portion 20 of the outer socket 12. The universal lock 18 includes a channel 22 extending axially there through for receiving the locking pin 16. Spring-loaded protections (not shown) within the channel 22 engage with the teeth 24 of the locking pin such that the projections and the shape of the teeth 24 allow the locking pin to be easily inserted within the channel 22 yet prohibit the locking pin from being extracted again from the channel 22. Accordingly, a spring loaded release mechanism 26 may be activated by the patient to disengage the projections within the channel 22 from the teeth, thereby allowing the locking pin to be extracted again from the channel 22. The universal lock 18 is one of may interconnection components that can be used with the prosthetic limb assembly. Other interconnection components, such as the interconnection component described in U.S. Pat. No. 5,662,715 to Slemker (commercially available as a "ProSeal" from Prosthetic Design, Inc.) may also be used.

The distal end 28 of the universal lock 18 has four threaded holes 30 which are aligned with the four holes extending through the distal end 32 of the outer socket. The holes are preferably arranged in an industry standard four-hole pattern. A titanium pyramidal link-plate 34 also includes four holes 36 which are to be aligned with the four threaded holes of the universal lock 18. Accordingly, four threaded screws 38 are used to attach the pyramidal link-plate 34 to the distal end wall 32 of the outer socket and simultaneously secure the universal lock 18 within the extended portion of the outer socket, sandwiching the distal end wall 32 between the universal lock 18 and the pyramid plate 34. A pyramid boss 40 formed integrally with the pyramidal link-plate 34 is provided to attach the upright assembly (not shown) of the prosthetic limb to the distal end of the prosthetic limb socket assembly 10.

The distal end wall 32 of the socket extension 20 is preferably perfectly planar (flat) so that when the bolts 38 tighten to couple the pyramid plate 34 to the socket 12 and correspondingly to the locking component 18, cold-flow damage to the socket 12 will be prevented. Additionally the planar end wall keeps the pyramid plate 34 and locking component 18 parallel to each other, which helps to keep the bolts 38 from binding also keeps the tightened bolts in pure tension. When the ProSeal component (described above) is used, the flat distal end wall 32 ensures even compression of the o-ring, creating a suitable seal.

Figure 2:
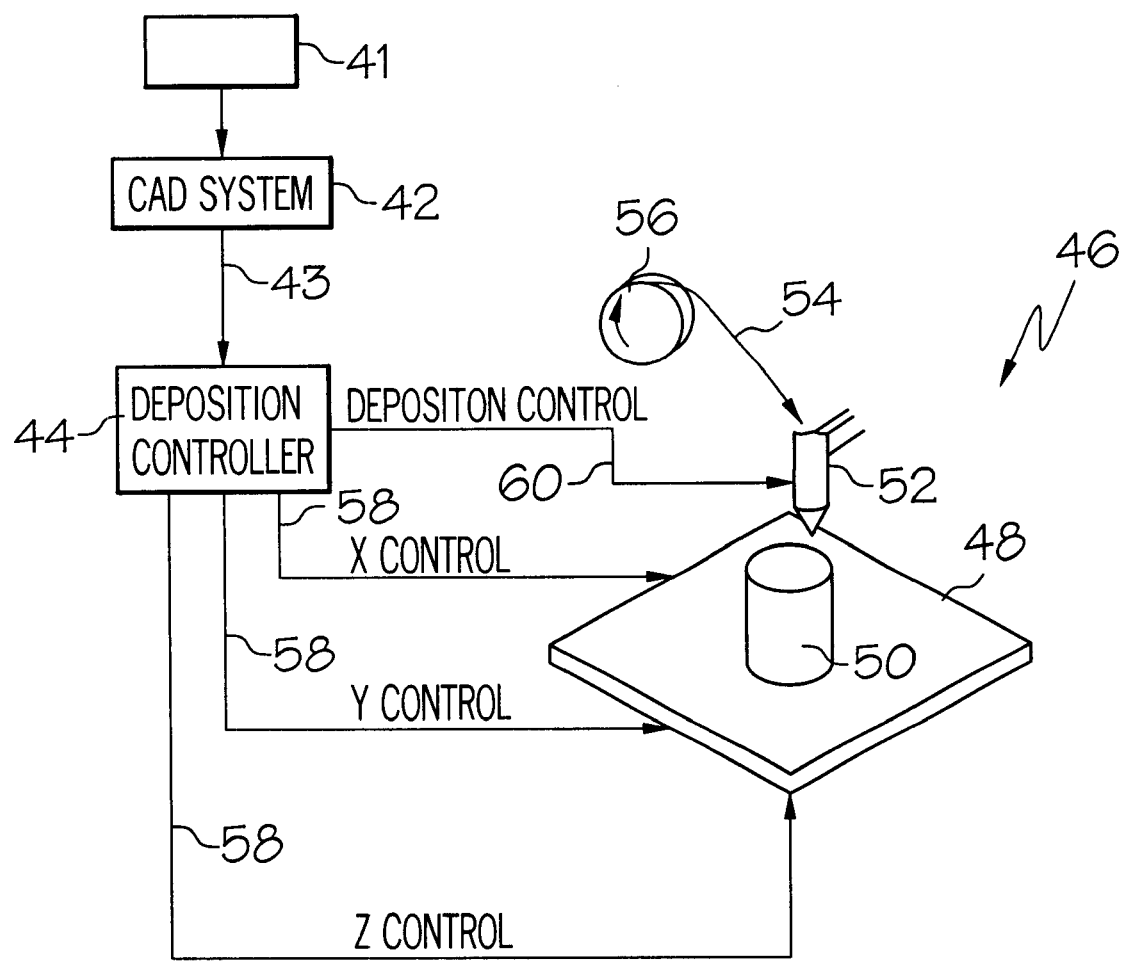
FIG. 2 is a schematic, block-diagram representation of a rapid manufacturing system for use with the present invention.

As shown in FIG. 2, the present invention facilitates a completely automated system for fabricating a prosthetic limb socket. A digitizing device 41 will first create a three-dimensional digital representation (dimensions) of the amputee's residual limb. This digital representation may include the outer surface dimensions of the residual limb, and may also include internal bone structure and muscle structure dimensions depending upon the complexity of the digitizing device used. This digital representation will then be fed into a computer aided design ("CAD") system 42, where a knowledge based computer program running on the CAD system will generate the digital dimensions 43 of the socket to be fabricated based upon the image of the residual limb. This program will preferably add the necessary biomedical modifications to the socket's digital dimensions, and will also incorporate the dimensions of the locking device 18 so as to form the extended portion 20 of the socket. Suitable digitizing devices and CAD systems for use with the present invention include the TraceCAD system, commercially available from Tracer Corporation, or the Benz CAD/CAM and Digitizing system, available through the Benz Group Limited.

Once generated, the modified socket dimensions 43 are then sent to the deposition controller 44 of a rapid manufacturing system 46. A suitable rapid manufacturing system for use with the present invention is commercially available from Stratasys, Inc. and is described in U.S. Pat. No. 5,121,329, the disclosure of which is incorporated herein by reference. Such a rapid manufacturing system creates three-dimensional objects based upon the digital dimensions supplied by the CAD system 42 by depositing multiple layers of solidifying material, which is initially in a fluid state, onto a platform 48 to build up a three-dimensional product 50 according to the dimensions 43 provided by the CAD system. Rapid manufacturing system 46 includes a dispensing head 52 for heating and liquefying thermoplastic material 54 supplied by a spool 56, and for depositing the heated liquified material onto the platform 48 which moves in the XYZ directions according to instructions 58 sent by the deposition controller 44. The deposition controller 44 also sends the deposition control instructions 60 to the nozzle dispensing head 52 so as to control the amount and timing of the material deposition. Other multi-layer rapid manufacturing systems are also known in the art and the present invention is intended for use with these multi-layer rapid manufacturing systems as well.

Figure 3:
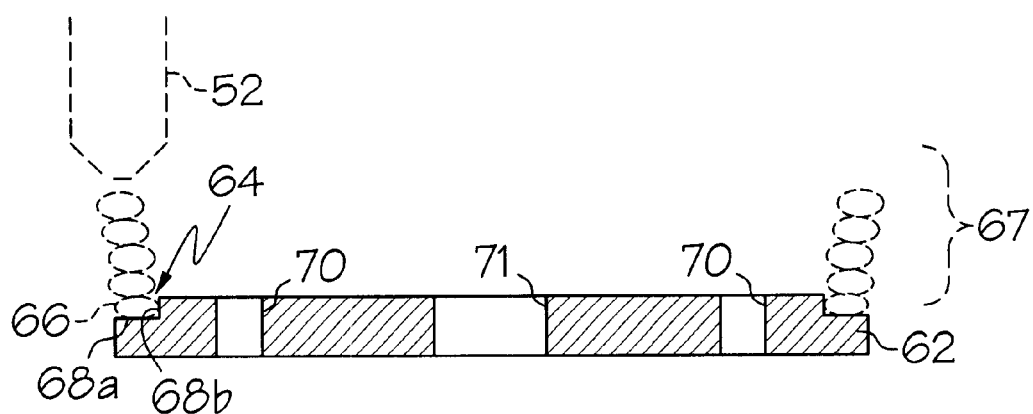
FIG. 3 is an elevational, cross-sectional view of an attachment plate of the present invention.
Figure 4:
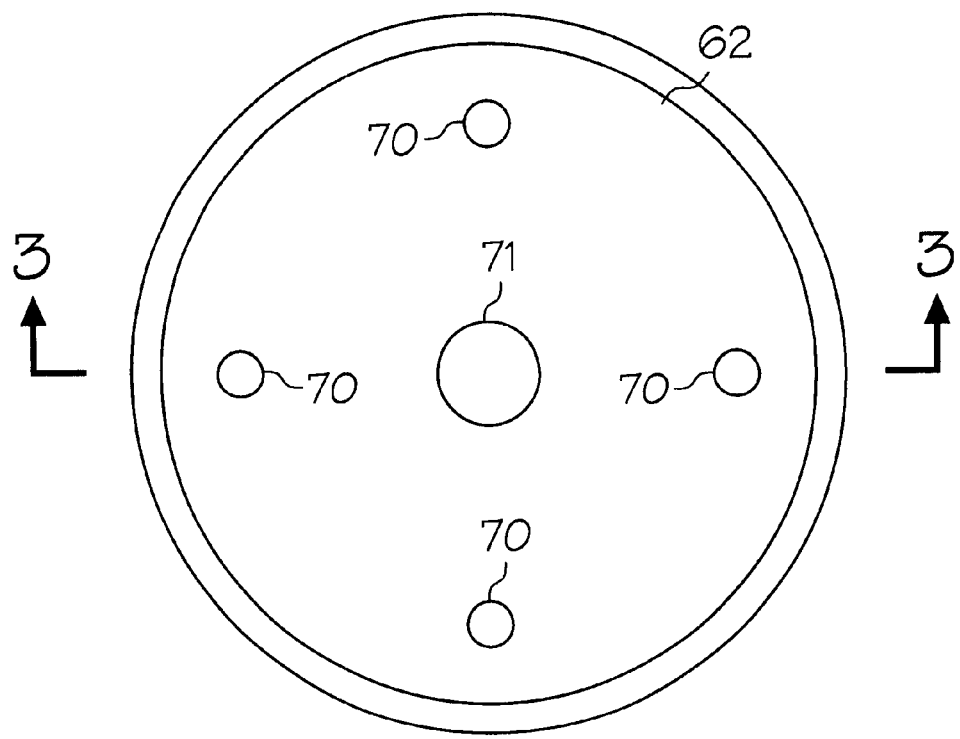
FIG. 4 is a top plan view of the attachment plate of FIG. 3.

As shown in FIGS. 3 and 4, an attachment plate 62 is provided for building a prosthetic limb socket thereon using the rapid manufacturing unit 46. Preferably, the attachment plate is disc shaped and includes a notch 64 machined or formed into the outer periphery of the attachment plate so as to receive a first layer 66 of the solidifying material. When the solidifying material is first layered into this notch 64, the layer will have two faces 68a and 68b of the notch to bond with, thus providing substantial structural support to the layers of material built up therefrom. Repeated layers 67 of the solidifying material will thereafter be built upon the first layer 66, controlled by the deposition controller 44, so as to form the socket as directed by the dimensions 43 sent by the CAD system 42. The attachment plate 62 also preferably includes a plurality of bolt receiving holes 70 bored axially therethrough for receiving the attachment bolts 38 as shown in FIG. 1, thus facilitating coupling of the upright assembly to the distal end of the socket (see FIG. 8) formed by the process of the present invention. The optional central hole 71 allows the locking pin 16 to extend therethrough if a universal lock 18 is used with the finished socket. Otherwise, the central hole 71 may be used as a fixturing hole. The attachment plate 62 (or at least the upper end of the attachment plate) is preferably formed or molded from a plastic material that sufficiently bonds to the first layer 66 of solidifying material deposited thereon.

Figure 5:
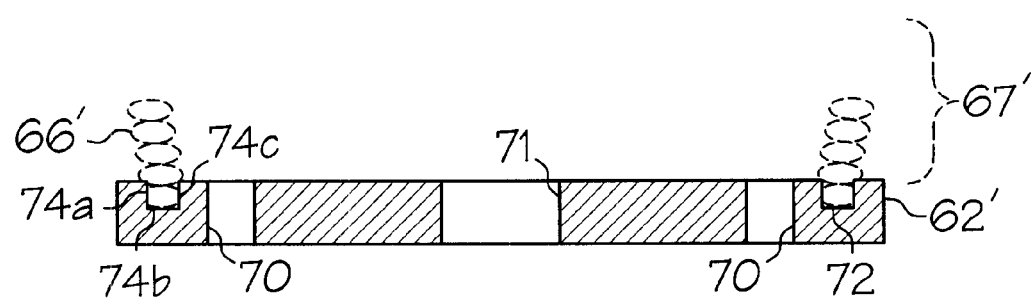
FIG. 5 is a cross-sectional, elevational view of another embodiment of an attachment plate of the present invention.
Figure 6:
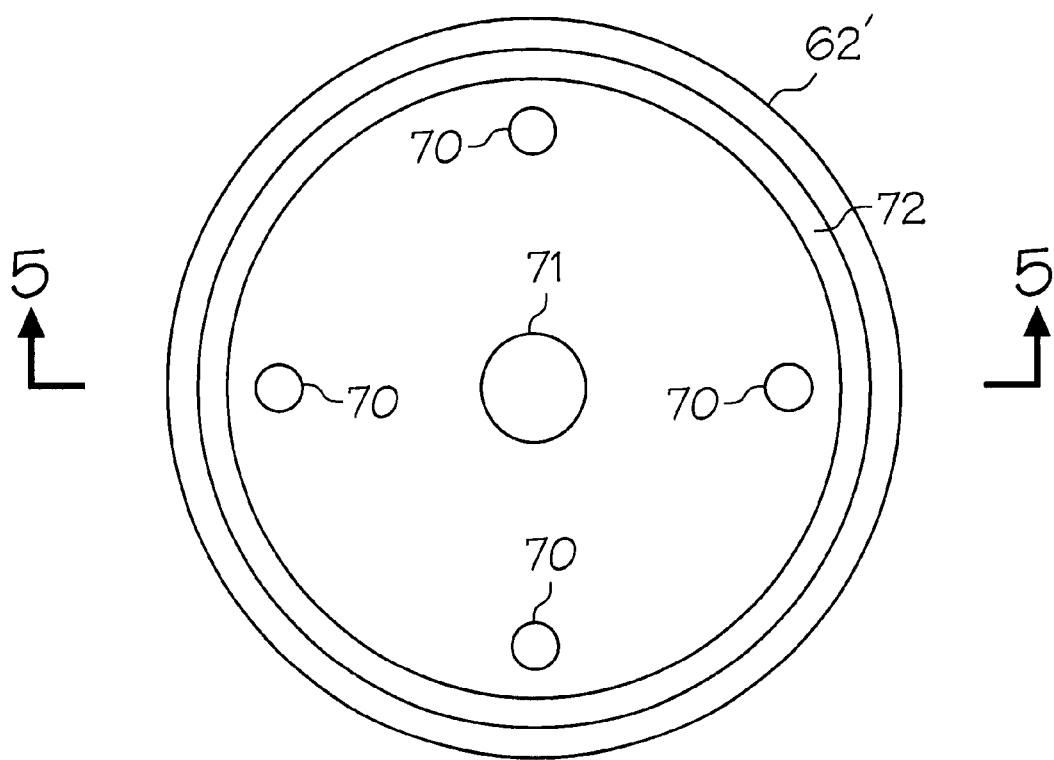
FIG. 6 is a top plan view of the attachment plate of FIG. 5.
Figure 8:
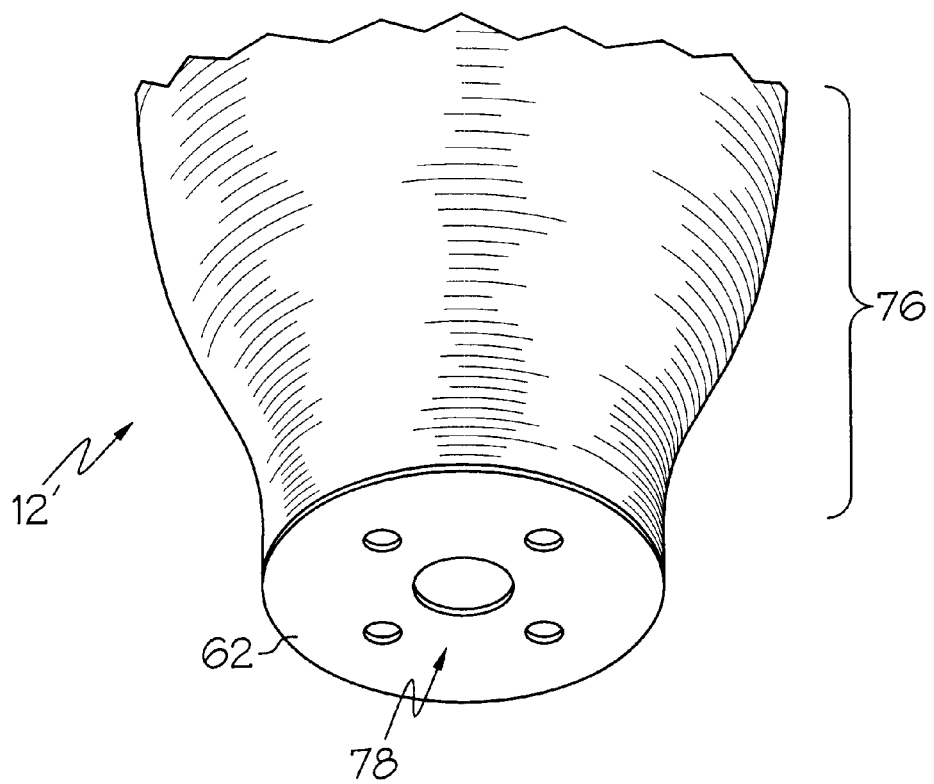
FIG. 8 is a perspective view of a socket fabricated according to a method of the present invention.

As shown in FIGS. 5 and 6, an alternate embodiment of the attachment plate 62' includes a substantially U-shaped notch 72 extending into the proximal surface of the plate and extending substantially about an outer periphery of the attachment plate. The first layer 66' of material will be preferably deposited within this notch 72 and will have three faces 74a, 74b and 74c of the notch to bond with, thus providing optimum structural support to the remaining portions 67' of the prosthetic limb built up therefrom. As shown in FIG. 8, when multiple layers 76 of the solidifying material are sequentially layered on top of each other under the control of the distribution controller 44 with regard to the dimensions of the socket 43, a socket 12' will be produced. Such a socket will have a substantially flat and rigid distal end 78 which is provided by the attachment plate 62 or 62'. The attachment plate 62 will also carry interconnection components (the bolt receiving holes 70) thereon so as to possibly eliminate the need for additional interconnection components to be provided within the interior of the socket.

Figure 9:
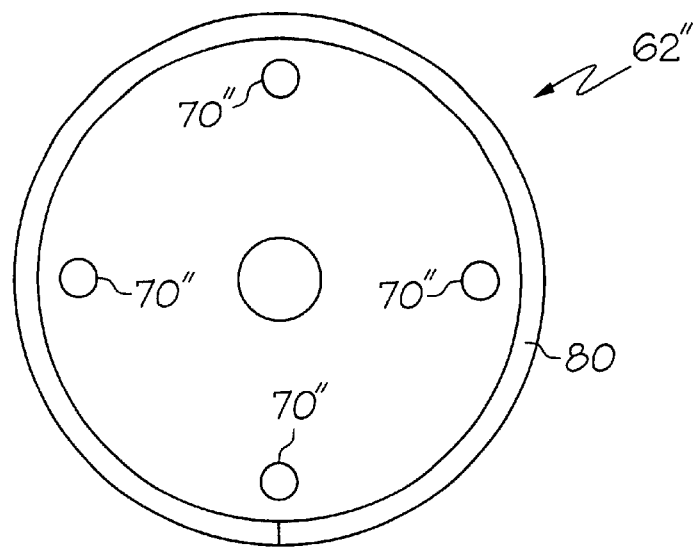
FIG. 9 is a top plan view of another embodiment of an attachment plate of the present invention.
Figure 10:
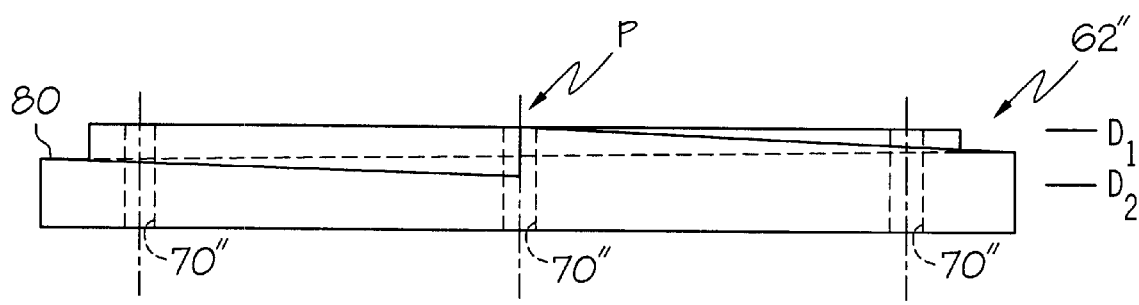
FIG. 10 is an elevational view of the attachment plate of FIG. 9.
Figure 11:
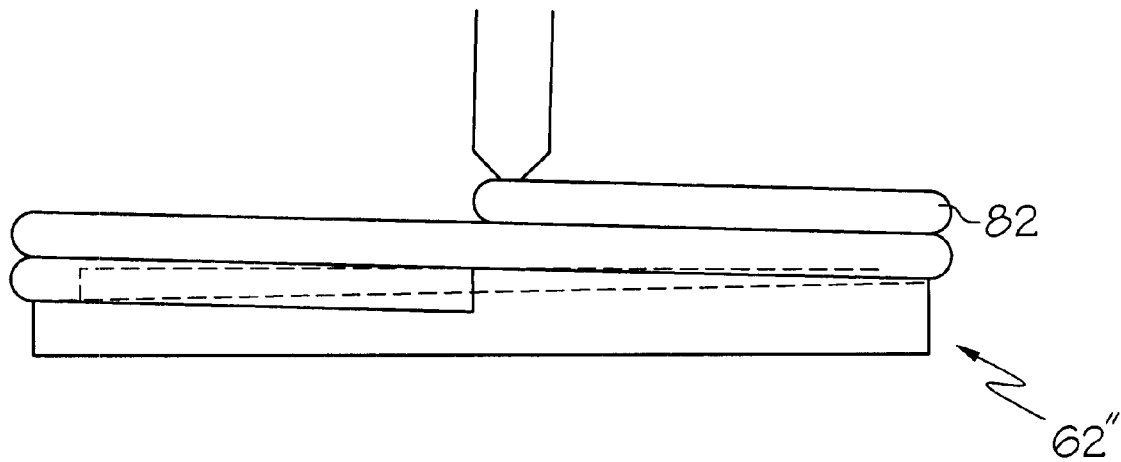
FIG. 11 is an elevational view of the attachment plate of FIGS. 9 and 10, including a layer of solidifying material deposited thereon.

As shown in FIGS. 9–11, another alternate embodiment of the attachment plate 62" includes a substantially helical notch 80 machined into the outer periphery of the attachment plate. The helical notch 80 starts at a circumferential point P at a first depth $D_1$ and ends at the circumferential point P at a second depth $D_2$. Accordingly, as shown in FIG. 11, the material deposited into the helical notch may build upon itself in a continuous helical layer 82. Preferably, the distance between the first and second depths $D_1$ and $D_2$ is substantially close to or the same as the height (or thickness) of the layer 82 of material being deposited.

Figure 12:
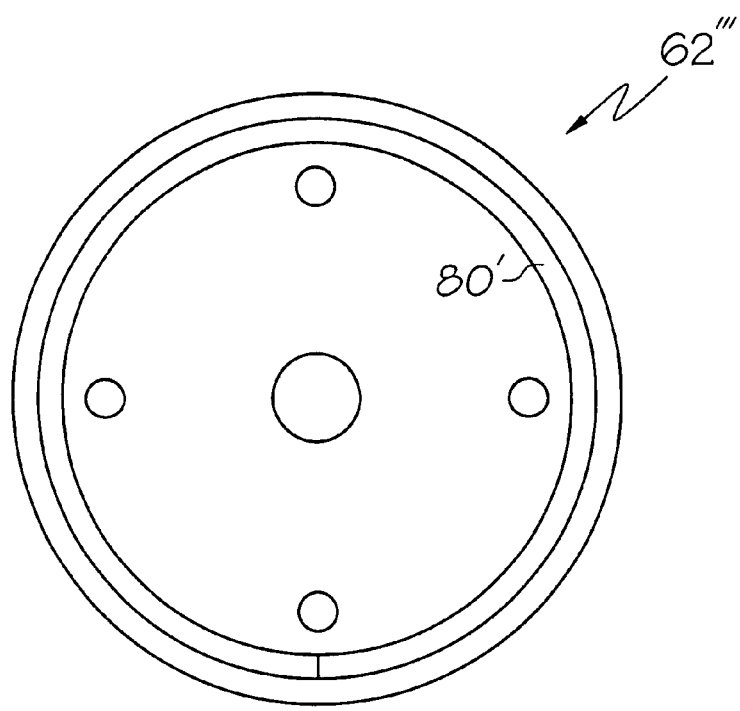
FIG. 12 is a top plan view of another embodiment of an attachment plate of the present invention.

Similar to the above embodiments, the attachment plate 62" also preferably includes a plurality of bolt receiving holes 70" bored axially therethrough for receiving the attachment bolts 38. In yet another embodiment of the attachment plate 62'", as shown in FIG. 12, the helical notch 80' is unshaped so that the layer 82 (not shown) of material deposited within this notch 80' and will have three faces of the notch to bond with.

Figure 7:
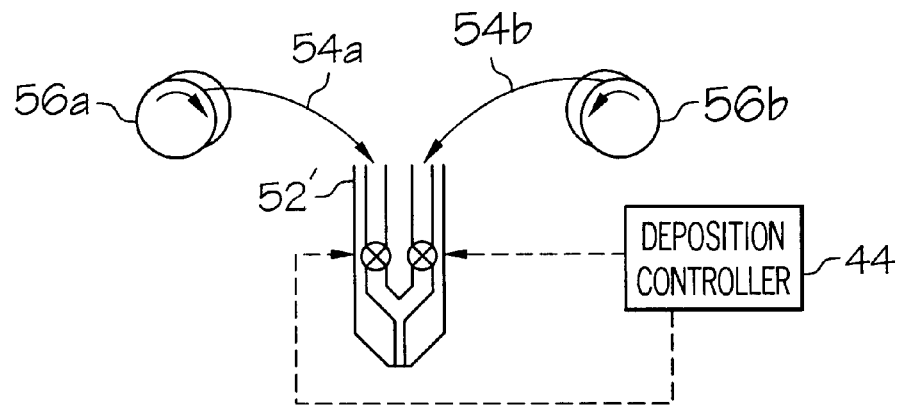
FIG. 7 is a schematic, block diagram representation of a rapid manufacturing unit utilizing two different types or grades of solidifying materials.

As shown in FIG. 7, another aspect of the present invention provides two different types or grades of dispensing materials 54a and 54b from separate spools 56a and 56b. The dispensing head 52' will individually liquify the materials 54a and 54b and will deposit either one the particular materials or a controlled combination of the two materials, under control of the deposition controller 44, depending upon the material properties required in a particular portion of the socket. Accordingly, one advantage for using the dual materials is that one of the materials can be a rigid material while the other material can be somewhat more flexible. Accordingly, if a large percentage of the flexible material is combined with a smaller percentage of the rigid material, flexible regions could be implemented into the socket during the fabrication process. Likewise, if a portion of the socket is to be substantially rigid, then more or all of the rigid material will be deposited. The positioning and deposition of these flexible regions can be controlled by the deposition controller according to the instructions provided by the CAD system. Additionally, such combination of materials may be controlled by a finite element analysis package that would create a finite model of the patient's limb data. This model would then be loaded into the CAD system in a manner that simulates normal gate activity to determine the high stress regions. Based upon this analysis, the materials could be combined in a manner that would optimize the strength of the socket in the regions requiring greater support and rigidness. Of course, it will be apparent to those of ordinary skill in the art that it is within the scope of the invention to utilize more than two different types or grades of dispensing materials, each providing a different rigidity, flexibility, thermal conductivity, comfort or other characteristic when solidified.

Figure 13:
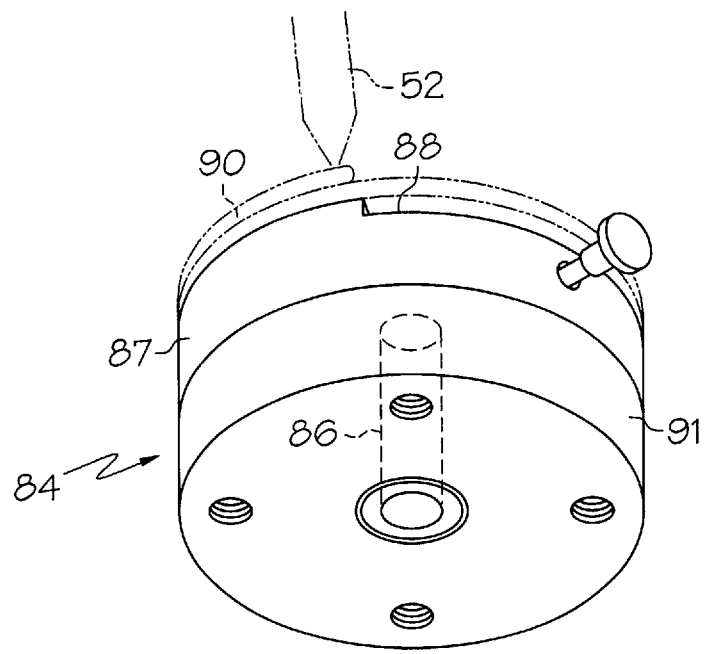
FIG. 13 is a perspective view of an attachment base of the present invention.

It is also within the scope of the invention that the attachment plates discussed above incorporate other interconnection or endoskeletal components as is known to those of ordinary skill in the art. While such attachment components may no longer resemble "plates," the term attachment plate will be used herein for continuity. As shown in FIG. 13 it is within the scope of the invention to provide an attachment plate in the form of a universal lock 84, having a channel 86 extending axially therethrough for receiving the locking pin of an inner sleeve component of a prosthetic limb assembly, where the universal lock 84 includes an upper plastic layer 87 having a notch 88 machined into its proximal surface so that multiple layers 90 (or a single layer, in the case of a helical notch) of the solidifying materials can be deposited thereon, thereby building the outer prosthetic limb socket up from the universal lock 84. The lower layer 91 of the universal lock may be made from any suitable material such as titanium, stainless or aluminum. Such a design will minimize profile or height of the prosthetic components coupled to the distal end of the patient's residual limb. This is a benefit if the patient has a long residual limb. If the patient is wearing an energy storing foot component (such as a Flex-Foot component), the lower profile maximizes the length and energy storing capability of the foot component.

Figure 14:
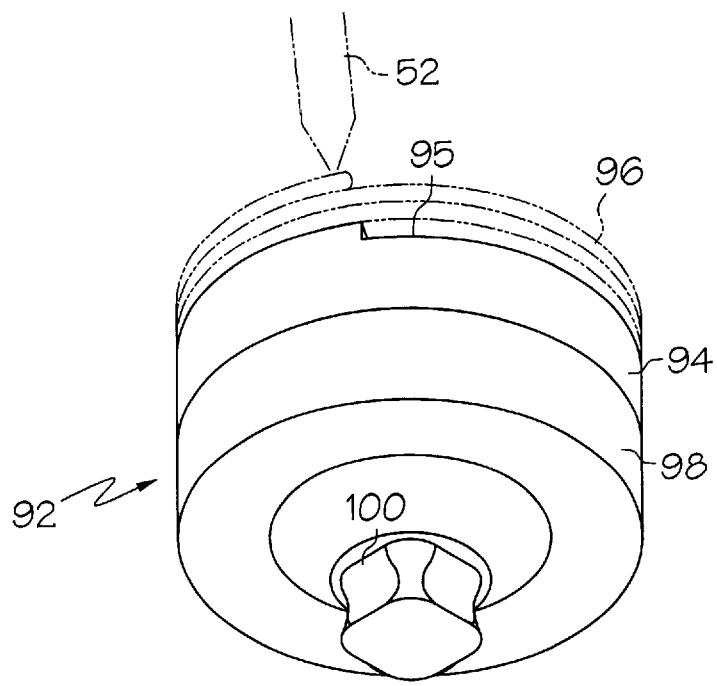
FIG. 14 is a perspective view of another embodiment of an attachment base.
Figure 15:
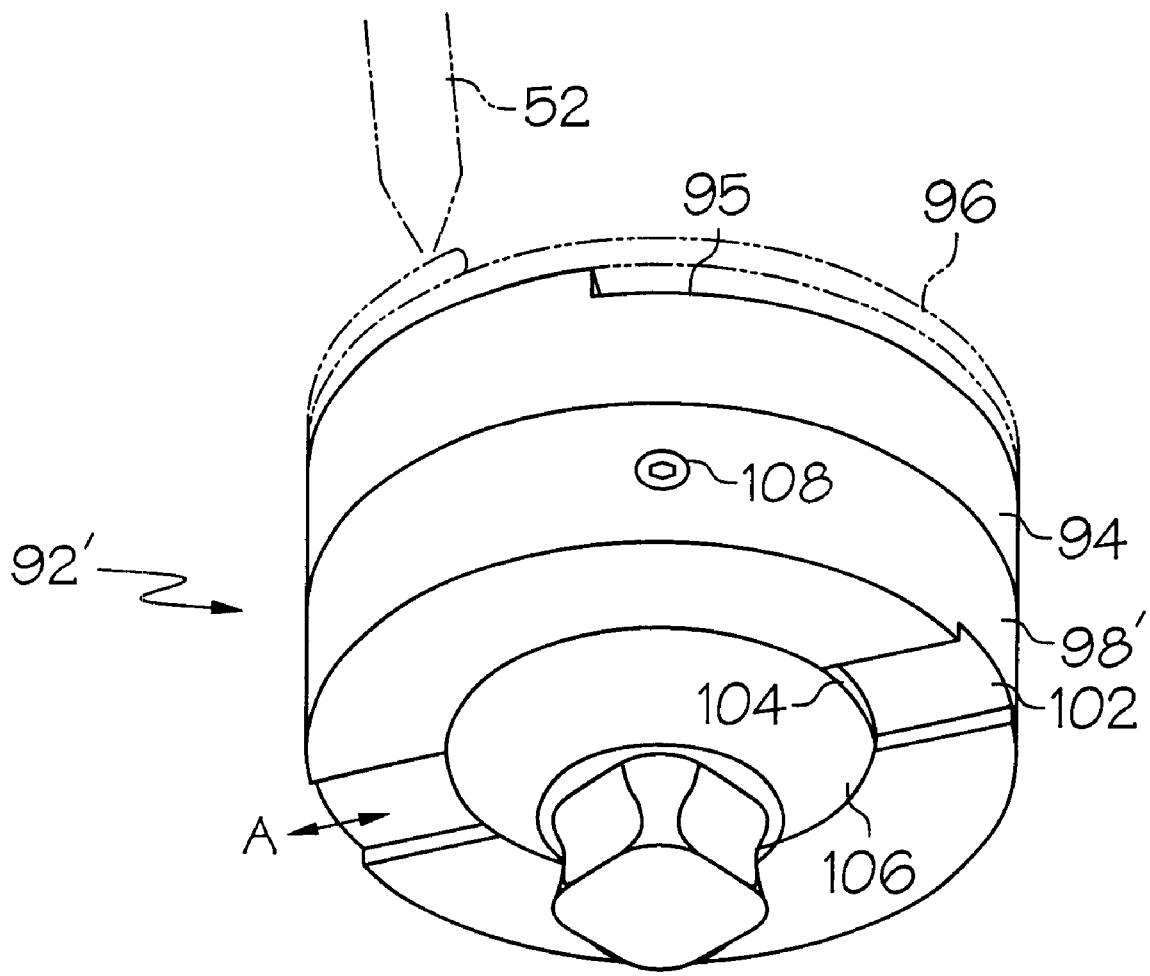
FIG. 15 is a perspective view of yet another embodiment of an attachment base.

As shown in FIG. 14, another example attachment plate component 92 incorporates the pyramidal link-plate 40 discussed above into the lower layer 98, minimizing the profile of the prosthetic components even more. The attachment plate component 92 includes an upper plastic layer 94 with a notch 95 machined or formed into its proximal surface so that multiple layers 96 (or a single layer, in the case of a helical notch) of the solidifying materials can be deposited thereon, thereby building the outer prosthetic limb socket up therefrom. The lower titanium layer 98 includes a pyramidal attachment link 100 integrally formed thereon. As shown in FIG. 15, an alternate embodiment of the component 92' includes a lower titanium layer 98' that has a dove-tail shaped groove 102 machined therein for slidably receiving a complimentary dove-tail shaped tooth 104 of a pyramidal attachment link component 106. Accordingly, the pyramidal link component is laterally adjustable in the directions indicated by arrow A. A mechanical lock, controlled by a set screw 108, locks the pyramidal link component in a lateral position when sufficient alignment is achieved.

Having described the invention in detail and by reference to the drawings, it will be apparent that modification and variations are possible without departing from the scope of the invention as defined herein.

What is claimed is:

1. A method for fabricating a socket component for a prosthetic limb comprising the steps of:
   (a) providing an attachment plate, the attachment plate including coupling means carried thereon for coupling a prosthetic limb upright assembly thereto, and the attachment plate including a proximal surface; and
   (b) repeatedly depositing layers of solidifying material to the proximal surface of the attachment plate so as to form a socket for receiving a patient's residual limb.

2. The method of claim 1, wherein the attachment plate includes a notch extending into the proximal surface and which extends about an outer periphery of the attachment plate; and step (b) includes a step of depositing at least one layer of the solidifying material into the notch; whereby the notch provides at least two faces for the one layer of solidifying material to bond with.

3. The method of claim 1, wherein the attachment plate is substantially planar and the coupling means includes at least one bolt-receiving hole bored vertically through the attachment plate.

4. The method of claim 1, wherein step (b) includes a step of depositing at least one layer of the solidifying material onto the proximal surface of the attachment plate in a substantially helical, vertical pattern.

5. The method of claim 1, wherein the solidifying material includes a first material that solidifies as a substantially rigid solid and a second material that solidifies as a solid which is more flexible than the solid of the first material; and step (b) includes a step of controlling the deposition of the first and second materials, separately or in combination, in portions of the socket depending upon endoskeletal or musculature characteristics of the patient's residual limb.

6. The method of claim 5, wherein a greater proportion of the second material is deposited in portions of the socket providing lesser support for the patient's residual limb.

7. The method of claim 6, wherein a greater proportion of the first material is deposited in portions of the socket providing greater support for the patient's residual limb.

8. The method of claim 1, wherein step (b) includes the step of controlling the deposition of the layers of solidifying material according, at least in part, to dimensions of a patient's residual limb.

\* \* \* \* \*